United States Patent [19]

Zohar

[11] Patent Number: 5,288,705
[45] Date of Patent: Feb. 22, 1994

[54] MANIPULATION OF OVULATION AND SPAWNING IN FISH

[75] Inventor: Jonathan Zohar, Eilat, Israel

[73] Assignee: Israel Oceanographic & Limnological Research Ltd., Haifa, Israel

[21] Appl. No.: 417,772

[22] Filed: Oct. 6, 1989

[30] Foreign Application Priority Data

Oct. 10, 1988 [IL] Israel ......................................... 87982

[51] Int. Cl.$^5$ ........................ A61K 37/02; C07K 7/06
[52] U.S. Cl. ..................................... 514/15; 530/327; 530/328
[58] Field of Search ................... 514/15; 530/327, 328

[56] References Cited

U.S. PATENT DOCUMENTS

| | | | |
|---|---|---|---|
| 4,255,420 | 3/1981 | Bergfeld et al. | 514/8 |
| 4,410,514 | 10/1983 | Vale, Jr. et al. | 514/15 |
| 4,443,368 | 4/1984 | Sherwood et al. | 530/334 |
| 4,647,552 | 3/1987 | Gulyas et al. | 514/15 |
| 4,659,693 | 4/1987 | Nestor | 514/13 |

FOREIGN PATENT DOCUMENTS 0232877 8/1987 European Pat. Off. .
0293632 12/1988 European Pat. Off. .

OTHER PUBLICATIONS

Chemical Abstracts Accession No. 110(12):101646; Sherwood et al., "Sustained hormone release, I, Characteristics of in vitro release of gonadotropinreleasing hormone analog (GnRH-A) from pellets" & Aquaculture, 74(1-2), 75-86.

Chemical Abstracts Accession No. 107(13): 109765; Fraser et al., "An implant of a Gonadotropin release hormone agonist (buserelin) which suppresses ovarian function in the macaque for 3-5 months", & Acta Endocrinol, (Copenhagen), 115(4) 521-527.

*Primary Examiner*—Merrell C. Cashion, Jr.
*Assistant Examiner*—S. G. Marshall
*Attorney, Agent, or Firm*—Foley & Lardner

[57] ABSTRACT

Administration into fish of gonadotropin releasing hormone (GnRH), luteinising releasing hormone (LHRH) and their analogs in a polymer based sustained release delivery system was found to induce a prolonged elevation in the fish's plasma level of gonadotropin (GtH), which leads to ovulation and spawning. Such induction of ovulation and spawning was found to occur both within the natural spawning season and outside this season. Such administration thus enables for the first time an effective means for manipulating reproduction in fish, which is a very important factor in the economic management of fish farming.

9 Claims, 1 Drawing Sheet

MANIPULATION OF OVULATION AND SPAWNING IN FISH

FIELD OF INVENTION

The invention is in the field of marine aquaculture and more specifically relates to hormonal treatment of fish in order to manipulate their reproduction.

BACKGROUND AND PRIOR ART

The following publications constitute a relevant prior art to the subject matter of the present invention:

1) Almendras, J. M., Duenas, C., Nacario, J., Sherwood, N. M., and Crim, L. W., 1987. In: "Proceedings of the Fish Breeding-Workshop". Singapore, April 7-10, 1987.
2) Crim, L. W. and Glebe, B. D., 1984. Aquaculture 43:47-56.
3) Crim, L. W., Glebe, B. D., and Scott, A. P., 1986. Aquaculture 56:139-149.
4) Crim, L. W., Sutterlin, A. M., Evans, D. M., and Weil, C., 1983. Aquaculture 35:299-307.
5) Goren, A., Zohar, Y., Koch, Y., and Fridkin, M., 1987. In: "Proceedings of the 3rd Int. Symp. on Reprod. Physiol. of Fish". St. John's, Newfoundland, August 1987.
6) Harvey, B., Nacario, J., Crim, L. W., Juario, J. V., and Marte, C. L., 1985. Aquaculture 47:53-59.
7) Lee, C. S., Tamarus, C. S., Banno, J. E., Felley, C. D., Bocek, A., and Wyban, J. A. (1986). Aquaculture 52:199-205.
8) Pankhurst, N. W., Van Der Kraak, G., and Peter, R. E., 1986a. Fish Physiol. Biochem. 1:45-54.
9) Pankhurst, N. W., Van Der Kraak, G., Peter, R. E., and Breton, B., 1986b. Fish Physiol. Biochem. 1:163-170.
10) Peter, R. E., Nahorniak, C. S., Sokolowska, M., Chang, J. P., Rivier, R. E., Vale, W. W., King, J. A., and Millar, R. P., 1985. Gen. Comp. Endocrinal. 58:231-242.
11) Petri, W., Seidel, R., and Sandow, J., 1984. In "LHRH and Its Analogues—Basic and Clinical Aspects" (F. Labrie, A. Belonger, and A. Dupont, eds.) pp. 63-76. Excerpta Medica Press.
12) Sanders, L. M., McRae, G. I., Vitale, K. M., Vickery, B. H., and Kent, J. S., 1984. In "LHRH and Its Analogues—Basic and Clinical Aspects (F. Labrie, A. Belonger and A. Dupont, eds.) pp. 53-62. Excerpta Medica Press.
13) Schally, A. V., 1978. Science 202:18-28
14) Sherwood, N., Eiden, L., Brownstein, M., Spiess, J., Rivier, J., and Vale, W., 1983. Proc. Natl. Acad. Sci. USA 80::2794-2798.
15) Stacey, N. E., Cook, A. F., and Peter, R. E., 1979. Gen. Comp.Endocrinol. 27:246-249.
16) Weil, C. and Crim, L. W., 1983. Aquaculture 35:103-115
17) Zohar, Y. and Gordin, H., 1979. J. Fish Biol. 15:665-670.
18) Zohar, Y., Breton, B., and Fostier, A., 1986. Gen. Comp. Endocrinol. 64:189-198.
19) Zohar, Y., Pagelson, G., Tosky, M., Finkelman, Y., and Shmuel, E., 1987. In: "Proceedings of the 3rd Int. Symp. on Reprod. Physiol. of Fish". St. John's, Newfoundland, August 1987.
20) U.S. Pat. No. 4,443,368
21) U.K. Published Patent Application No. 2152342
22) U.S. Pat. No. 4,410,514
23) Japanese Published Patent Application No. 80-40210
24) Lin, H. R., Peng. C., Van der Kraak, G., Peter, R. E., and Breton, B., 1986. Gen. Comp. Endocrinol. 64:389-395
25) Peter, R. E., Nahorniak, C. S., Chang, J. P. and Crim, C. W. 1894 Gen. Comp. Endocrinol. 55:337-346
26) Peter, R. E., Lin, H. R. and Van der Kraak, G., 1984. In PROCEEDINGS OF THE FISH BREEDING WORKSHOP, Singapore, Apr. 7-10, 1987. Aquaculture 74:1-10
27) Sherwood, N. M. and Harvey, B. 1986. Gen. Comp. Endocrinol. 61:13-19.

Marine aquaculture in general, and fish farming in particular, has been extensively developed in recent years. While there has been considerable success in achieving high yields in rearing fish, there has been only limited success in the manipulation of the reproductive cycles of the reared fish. Such manipulation is a prerequisite for the further development of fish farming into a major agricultural industry.

Many of the economically important fish do not reproduce spontaneously in captivity. This is the case with mullet (*Mugil cephalus*), rabbitfish (*Siganus sp.*), milkfish (*Chanos chanos*), striped bass (*Morone saxatilis*), sea bass (*Dicentrarchus labrax*), seabream (*Sparus aurata*), catfish (*Clarias sp.*) and others. In all these species the reproductive failure is located in the female: whereas vitellogenesis is completed, the stages that follow, namely oocyte maturation and ovulation, do not occur, and thus there is no spawning. Instead, vitellogenic follicles undergo rapid atresia.

In some fish species which do ovulate spontaneously in captivity, such as trout and salmon, both Atlantic and Pacific, e.g. Atlantic salmon (*Salmo salar*) and Pacific salmon (*Onchorhynchus sp.*), ovulation is not synchronized and thus egg collection is a very laborious task. Additionally, the subsequent hatching of the fingerlings is not synchronized and therefore the ability to create schools of fingerlings being all at about the same growing stage, which is necessary for economical feasible fish farming, becomes very difficult.

In fish indigenous to temperate zones, such as seabream, seabass, cyprinids and salmoneds, reproduction is seasonal, i. e. ovulation and subsequent spawning occur once or several times during a limited season. Inducing such fish to ovulate and spawn out of the natural spawning season might largely contribute to the management of fish farming. For one, out of season egg production will enable full utilization of the fish farm throughout the whole year, since only thereby will it be possible to have at any given time fish of all ages and thus be able to market adult fish year round.

In salmoneds smoltification is also seasonal and in some species occurs a year or more after hatching, resulting in $S_1$ and $S_2$ smolts ($S_1$ and $S_2$ smolts - smoltification occurs more than 1 year and 2 years after hatching, respectively). It may be induced earlier in the fish's life if the brood fish are induced to spawn out of the natural spawning season, which, if feasible, will have important economic consequences. Thus, for example, in various salmon species, e.g. the Pacific salmon and the Atlantic salmon, before season spawning might result in a high proportion of $S_0$ and $S_1$ smelts ($S_0$ smelts - smoltification occurs less than a year after hatching) and as a consequence a shortening of the period during which the fingerlings are stocked in fresh water hatchery facilities. This means a very significant saving in facilites, feed and manpower, as well as an earlier acceleration of growth rate (upon transfer of the fingerlings into sea water, their growth rate is accelerated), all of which will bring about a total reduction in the expenses related to the farming of the fish.

In many salmon hatcheries eggs are obtained from captured adults returning from the sea for reproduction. However, the egg yield is usually low since many adults return early, i.e. before they are ready to spawn, and die in captivity before spawning. The yield may be increased significantly if these early refuming adults were induced to ovulate earlier.

Ovulation and spawning in female fish are controlled by pituitary hormones, mainly the gonadotropins (GtH). However, the release of GtH is not spontaneous but rather induced by a gonadotropin releasing hormone (GNRH) which is secreted by the hypothalamus. The GriRH was found to be a decapeptide both in mammals (Schally, 1978) and in fish (U.S. Pat. No. 4,443,368). It has recently been found in female Sparus aurata, that the level of GtH in the pituitary gland increases as the fish approaches its natural spawning season, i.e. winter time. However, this accumulated GtH is not released into the blood, the consequence being that the oocytes undergo rapid atresia. In cases where ovulation and spawning do occur, this is always accompanied by a GtH surge in the blood (Stacey et al., 1979; Zohar et al., 1986, 1987). Such a surge of GtH and the subsequent ovulation and spawning may be induced by injection of GNRH or analogs thereof. The use of natural fish GNRH in inducing ovulation and spawning have been described in U.S. Pat. No. 4,443,368 and the use of various analogs thereof has been described in U.K. Published Patent Application No. 2152342 and in U.S. Pat. No. 4,410,514. The use of luteinizing hormone releasing hormones (LHRH) for inducing spawning in fish has been described in Japanese Published Patent Application 80-40210.

The known methods for inducing ovulation and spawning in fish in accordance with the prior art usually involve injecting a saline solution containing a non-toxic salt of GNRH or analogs thereof into the fish. However, due to a short lifetime of the GNRH in the blood, the effect of such a treatment is minimal and in many fish species ovulation and spawning cannot be induced. For example, a single injection of a GNRH analog at an amount of 5-10 82 g/kg body weight, induces spawning in Sparus aurata, but only in as little as 20 to 30% of the GnRH-treated females (see the experimental section of this specification). The same phenomenon was found also to occur in other fish in which there is a non-synchronous ovarian development in captivity, such as the sea bass Lates calcarifer (Almendras, et al., 1987).

It should be noted that in many fish carrying out successful injections, in accordance with the prior art, requires highly skilled personnel since in many cases, prior to injecting, the development stage of the oocytes has to be determined. This determination involves withdrawing some oocytes using a capillary which is inserted into the oviduct and then examining the so withdrawn oocytes under a microscope. Skilled personnel needed therefor are not available in most fish farms and thus the yield of success in inducing spawning will be lower than that obtained in the laboratory, e.g. in the case of Sparus aurata spawning will be induced in less than 20% of the females.

The short lifetime of GNRH in the blood is partially due to its rapid degradation by both specific endopeptidases and non-specific exopeptideases present in the pituitary, kidney and liver (Goren, et al., 1987). The degradation generally occurs at positions 5-6 and 9-10 of the decapeptides. Therefore, substitution of the amino acid located at position 6 (glycine) by certain D-amino acids results in GNRH analogs which are less susceptible to enzymatic degradation, thus prolonging their presence in the blood and hence their biological effectiveness (Peter et al., 1985; Zohar et al., 1987; Goren et al., 1987). However, even such analogs, when injected in biological effactive amounts, still disappear from circulation quite rapidly e.g., 30 to 60 min. in goldfish (Sherwood and Harvey, 1986) and 1 to 2 hours in the seabream (Zohar, unpublished results). Thus, using cleavage resistant analogs by itself is insufficient for obtaining a long lasting release of GtH from the pituitary.

one way to overcome this limitation and to obtain a long lasting Surge Of GtH in the blood is to use multiple injections of GNRH. or analogs thereof, but such multiple injections are excluded in most fish species due to the stress they involve. It has also been proposed to apply GNRH through the water in which fish are kept, but such an application is not economical for large scale, agricultural, applications.

Another approach in obtaining a long lasting surge of GtH in the blood is to administer GNRH to the fish in a sustained release delivery system and this has indeed been reported. The use of silastic implants (silicone rubber impregnated with the active compound) containing super-active mammalian GNRH analogs was shown to increase plasma GtH levels and accelerate spawning (Crim et al., 1986) and also to accelerate spermiation (Weil and Crim, 1983) in the Atlantic salmon. However, such an implant was found to be non-effective in many fish such as the female Walleye (Pankhurst et al., 1986a), in the male goldeye (Pankhurst, et al., 1986b) and in Sparus aurata (see the experimental section of this specification).

Cholesterol pellets (which are also a sustained release delivery system) containing different agonists of mammalian GNRH were successfully used to accelerate or induce ovulation and/or spawning in a number of fish such as rainbow trout (Crim et al., 1983), Atlantic salmon (Crim and Glebe, 1984), sea bass (Harvey et al., 1985) and milkfish (Lee et al., 1986). However, in addition to the fact that the preparation of the cholesterol pellets is time consuming and not practical on an industrial scale, it does not give rise to an effective manipulation reproduction.

Polymer based sustained release delivery systems for administering GNRH have been used in mammals in general and in humans in particular, with biodegradable polymers as the delivery vehicle (Sanders et al., 1984; Petri et al., 1984). However, the use of such polymer based sustained release systems in fish has not yet been reported.

OBJECT OF THE PRESENT INVENTION

The object of the present invention is to overcome the limitations of the prior art and provide means for effectively manipulating reproduction in fish.

GENERAL DESCRIPTION OF THE INVENTION

In accordance with the invention it was found that reproduction can be manipulated very effectively if GNRH is administered to the fish in polymer based sustained release compositions. Such administration was found to bring about a long lasting increase in the plasma level of GtH and consequently ovulation and spawning.

The present invention thus provides a composition for the manipulation of reproduction in fish, which comprises an effective amount of an active compound selected from the group consisting of GNRH, LHRH, GNRH analogs, LHRH analogs and non-toxic salts of any of those compounds, embedded in a biocompatible sustained release polymer-based carrier matrix.

The term "sustained release" is understood to mean a gradual release of the active compound in a controlled mazmer. A suitable carrier having such sustained release properties may be chosen on the basis of its gradual release properties in a solution designed to resemble a fish's plasma, such as a ringer solution, other physiological saline solutions, fish serum, etc.

Manipulation of reproduction is understood to mean induction of ovulation and spawning in fish which do not reproduce spontaneously in captivity; synchronization of ovulation and spawning in other fish; as well as advancement and phase shift of ovulation and spawning in fish in which reproduction is seasonal.

The long lasting increase in plasma GtH levels in fish administered with sustained release compositions of said active compound is very surprising against the background of the hitherto known effect of such compositions in mammals in general and in humans in particular. GNRH and LHRH in mammals stimulate the release of luteinizing hormone (LH) and follicle stimulating hormone (FSH) from the anterior pituitary. While a single or a repetitive intermittent administration of these hormones or their analogs induces a pulsatile release of LH and FSH shortly after each injection, continuous infusion of these active compounds or their administration in a sustained release composition desensitizes the pituitary gonadotrophs so that LH and FSH secretion decreases considerably or even stops. In fact, sustained release compositions of GNRH, LHRH or analogs thereof are effectively used in medicine for treatment in cases of excess release of LH or FSH, such as in the treatment of precocious puberty.

The polymer based carrier matrix may comprise natural or synthetic polymers or copolymers. Examples of natural polymers are polysaccharides and various proteins. Synthetic polymers or copolymers may either be biodegradable, in which case the sustained release is due to biodegradation, or non degradable, in which case the sustained release is due to gradual diffusion of the active compound therefrom. Examples of biodegradable polymers and copolymers are polylactic polyglycolic acid, polyanhydrides, polyorthoesters and polycaprolactone. Examples of non biodegradable polymers are silicone rubber in a mixture with a relatively large amount of a biocompatible protein, a copolymer of ethylene and vinyl acetate, the relative amount of vinyl acetate being about 20-50%, and various synthetic polysaccharides. In general, any biocompatible polymeric controlled release carrier such as those hitherto used in the art for delivering GNRH or LHRH may in principle be used in accordance with the present invention.

The compositions of the present invention are solid and may be prepared in any suitable form such as pellets, discs, rods or microspheres. These may be administered to the fish either by implantation of a composition unit (in the form of a pellet, disc or rod) or by injection, either intramuscular, subcutaneous or intraperitoneal (in the form of a suspension of mini-rods or microspheres).

The size of an implantable composition in accordance with the present invention will be determined both by the size of the fish in which implantation thereof is intended, i.e. it should not be too big, and by practical limitations, i.e. the implantable composition should not be too small so as to render it difficult for manipulation. Thus, for example, a disc having a diameter of about 2-10 mm and a thickness of about 1-2 mm was found to be suitable for implantation in many fish such as the sea bream, sea bass and trout. Similarly, rods being 3-7 mm long and having a crosssectional area of about 1 mm$^2$ were also found to be suitable for implantation.

Injectable compositions in accordance with the invention in the form of mini-rods or microspheres should be sufficiently small to pass through a syringe. Injectable compositions will be suspended in an injectable solution, such as saline or various buffers, prior to injection.

The active compounds in the compositions of the present invention may be the native GNRH and LHRH which were disclosed as effective fish spawning inducers in U.S. Pat. No. 4,443,368 and Japanese Published Patent Application No. 80-40210, respectively.

As mentioned above, native GNRH is susceptible to rapid degradation in the blood due to cleavage of the decapeptide particularly at positions 5-6 and 9-10. Analogs having different amino acids at the relevant position which renders them less sensitive to such enzymatic degradation are thus preferred for use in the compositions according to the present invention although their use is not material to the present invention. Examples of such analogs are those substituted at positions 6 and/or 10 as well as others such as those disclosed in U.K. Published Patent Application No. 2152342 and in U.S. Pat. No. 4,410,514.

Implantable compositions in accordance with the invention may preferably comprise about 10-300 µg of the active compounds per unit. When administering an injectable composition in accordance with the invention, the administered composition will preferably comprise about 10-200 µg of the active compound per kg of body weight of the injected fish. The amount of the active compound may in some cases be reduced if a very super active analogue is utilized.

It is known in the art that the release of GtH in fish is regulated both by stimulatory GNRH and also by an inhibitory factor which is most probably dopamine. (termed also gonadotropin-release inhibitory factor, GRIF, Peter et al., 1984; Lin et al, 1986). In some fish species, such as cyprinids (Peter et al, 1987), the dopaminergic inhibitory effect on gonadotropin-release is dominant and hence in such cases the compositions in accordance with the present invention should also contain dopamine antagonists such as pimozide or domperidone.

The present invention also provides a method for the manipulation of reproduction in fish which comprises administering a substance selected from the group consisting of GNRH, LHRH, GNRH analogs, LHRH analogs and non-toxic salts of any of those compounds in a polymer-based carrier matrix as defined above. Where it is desired to induce or synchronize the ovulation and spawning within the natural spawning season, only the females will be so treated, since the males are usually ready to spermiate throughout this season. Where, however, it is desired to induce early ovulation and spawning, i.e. outside the natural spawning season, also the males will be treated. For such a treatment, the fish are slightly anesthetized and a composition in accordance with the present invention is then applied.

The composition may be administered to the fish either by subcutaneous or intra-peritoneal implantation (for implantable pellets, discs or rods) or by injection (for injectable micro-rods or spheres). For subcutaneous implantation a small incision is made through the fish's skin at a suitable place and after separating the skin from the underlying muscles, e.g. by the use of forceps, the implant is appropriately placed; for intraperitoneal implantation an incision is made through the skin and muscle of the peritoneal cavity and the implant is inserted through the incision and placed in the peritoneum. The incision in each case is made as small as practicably possible and there is usually no need for post implantational stitching.

For injection, the micro-rods or micro-spheres are suspended in a vehicle solution and thereafter the suspension is injected into a suitable muscle of the fish or into the peritoneal cavity.

The method of administering GNRH in accordance with the present invention yields highly superior results in effectively manipulating reproduction than results hitherto obtained in the art. Furthermore, the method of the invention is simple to perform, such that there is no need for prior determination of the oocytes' maturity stage which, as mentioned above, is required in accordance with prior art methods of injection of GNRH solutions.

All these improvements over the prior art are achieved by the fact that the surge in GNRH and the consequent surge in GtH is not temporary but rather long lasting.

After administering the composition, female fish are kept together with one or more spermiating males in containers until the spawned and fertilized eggs may be collected, which eggs are then kept in appropriate containers until hatching. The eggs so obtained also constitute an aspect of the present invention.

If all fish in a school intended for reproduction are treated by the method of the invention at about the same time, the resulting ovulation and spawning will be essentially synchronous, and thus collecting of the eggs is much easier and more economical than collecting the eggs in fish induced to spawn as hitherto performed in the art. Additionally, it will subsequently become much easier to form schools of fingerlings being all about the same age. Furthermore, in many fish species it will be possible to obtain such schools throughout the whole year, which was hitherto not possible.

It may be seen from all the above that the present invention enables, for the first time, an effective manipulation of reproduction in fish, which is highly significant in improving the economic management of fish farming.

DESCRIPTION OF SOME EMBODIMENTS

The following description exemplifies experiments performed in order to test the efficacy of the method and composition in accordance with the present invention in inducing gonadotropin-release and in inducing and synchronizing ovulation and spawning in three farmed fish species: gilthead seabream, sea bass and rainbow trout.

A man of the art will readily appreciate, that the invention is not limited to these specific examples but rather these are meant to illustrate the present invention and various modifications within the framework of the present invention as encompassed by the claims, are possible.

EXAMPLE 1

Female seabream (Sparus aurata) reaching final stages of vitellogenesis received one of the following treatment of GnRHa - an analog of mammalian GNRH ([D-Ala$^6$-Pro$^9$-NET]-LHRH):

1. An intramuscular injection of GnRHa in a saline solution (10 µg GnRHa/kg body weight which is an acceptable amount for injection);
2. Implantation of a Silastic implant (Sila.) according to Crim et al., 1986, containing GnRHa (150 µg GnRHa/fish);
3. Implantation of a biodegradable copolymer of polylacticpolyglycolic acid (Z. implant) containing GnRHa (150 µg GnRHa/fish);
4. Placebo injection of saline (Control).

Before the treatment and at various intervals thereafter, the fish were bled. After withdrawing a blood sample the fish were returned into the water. GtH levels were determined in the withdrawn blood sample by specific homologous radioimmunoassay. The results are shown in FIG. 1 of the annexed drawings.

Additionally, several treated, non-bled females from each treatment group were kept, each in a separate container, which was connected to an egg collector, together with two males. The females were followed for their spawning activity, which was defined in this experiment as tens of thousands of fertilized eggs collected per day over a period of more than one week.

Figure 1:
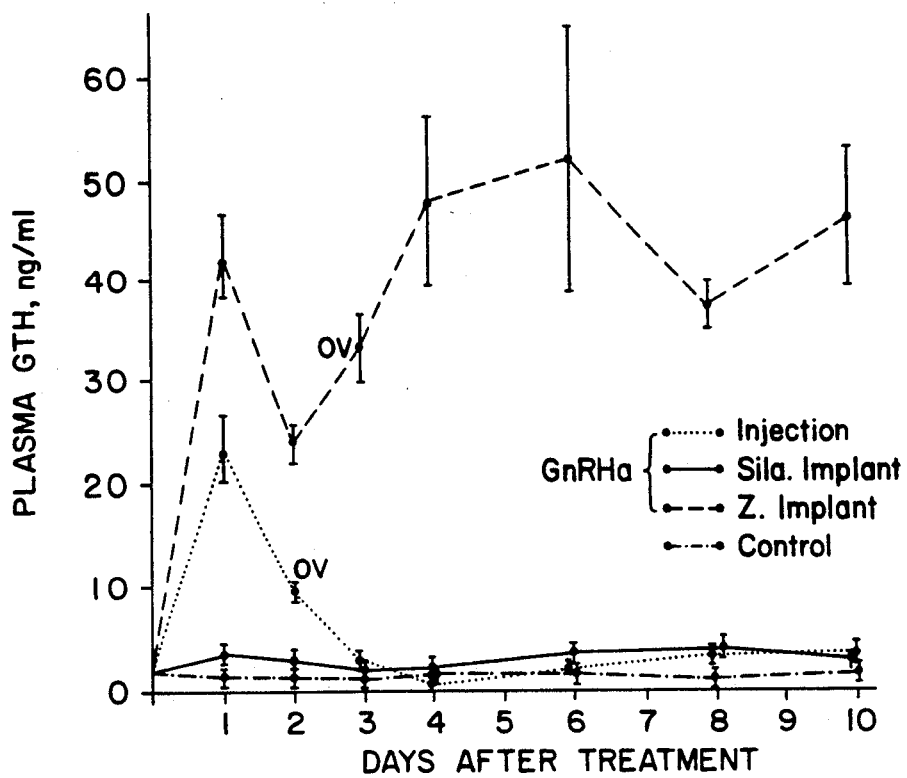
FIG. 1 shows the plasma levels of GtH in the female *Sparus aurata* prior to and at different times after the administration of a GNRH analog by various modes: Sila. implant - in a silastic implant; Z. implant - in a biodegradable copolymer of polylactic-polyglycolic acid; Injection - of GNRH analog dissolved in saline; Control - injection of saline.

It may be seen in FIG. 1 that practically no GtH release is seen in the female fish receiving treatment No. 2, similarly as those receiving treatment No. 4 (control). In agreement thereto, no spawning activity was observed in these two groups of fish.

In contrast to Group No. 1, in which the post injection GtH level decreased rapidly, the level in fish of Group No. 3 remained high over a prolonged period, well over 10 days. In agreement with this result, percentage of the females of Group No. 3 showing spawning activity was 80%, as compared to 25% in those of Group No. 1 and, additionally, the spawning activity lasted over a longer period than in Group No. 1.

The above results clearly demonstrate that best results are achieved when GnRHa administration is performed in accordance with the method of the present invention.

EXAMPLE 2

The efficacy of additional polymers to the one used in Example 1, as delivery systems for GNRH analogs in accordance with the invention, for the induction of GtH release, ovulation and spawning in the sea bream (Sparus aurata) was tested. The following combinations of polymers and GNRH analogues were tested:

1. Implantation of rods (about 3 mm long and about 1 mm$^2$ n cross-sectioned area) of polylactic polyglycolic acid containing 200 μg of [D-Ala$^6$-Pro$^9$-NET]-LHRH (ZIP).
2. Implantation of discs (about 6 mm in diameter and about 1 mm thick) of ethylene vinyl acetate copolymer (EVAC) containing 200 μg of [D-Ala$^6$-Pro$^9$-NET]-LHRH (KALA).
3. Implantation of a disc as in 2, above, but the active compound being [D-Arg$^6$-Pro$^9$-NET]-sGnRH (KARG).
4. Injection in saline of microspheres of polylactic polyglycolic acid containing 200 μg/fish of D-Trp$^6$-LHRH (TRP).

The control treatment consisted of application of EVAc implant which did not contain a GNRH analogue.

Figure 2:
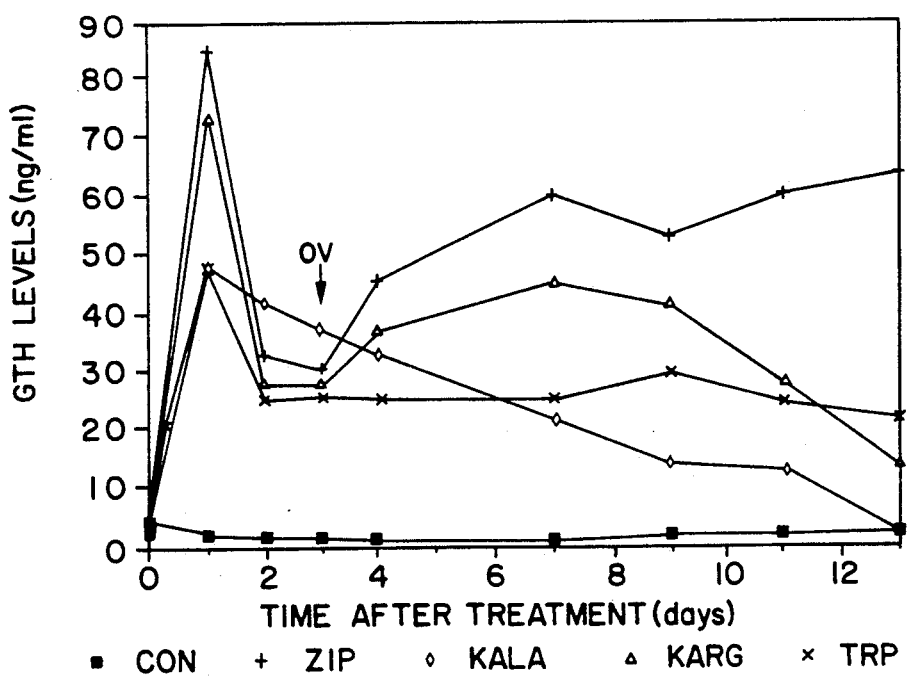
FIG. 2 shows the GtH levels in the female *Sparus aurata* before and at different times after the administration of different controlled-release delivery systems containing GNRH analogs: biodegradable copolymers of polylacticpolyglycolic acid ("ZIP" and "TRP"); ethylene vinyl acetate copolymers (KALA and KARG).

The results are shown in FIG. 2 of the annexed drawings.

It may be seen that all four delivery systems being in accordance with the present invention are effective in inducing increase in plasma GtH levels over prolonged periods of time.

EXAMPLE 3

A similar experiment as in Example 1 was performed, using, however, a different species of fish - sea bass, (Dicentrarchus labrax), instead of the seabream, and following the fish only for their spawning activity.

Similar results to those reported in Example 1 were obtained.

EXAMPLE 4

24 females of rainbow trout, Salmo gaixdneri, were divided into four groups, six fish in each group. Each group received one of the following treatments:

1. Injection of the mammalian GnRHa as in Example 1 (20 μg/kg body weight), in saline;
2. Administration of a biodegradable copolymer of polylactic-polyglycolic acid containing the same GnRHa (150 mg/fish 150 μg/fish) in pellets, implanted under the fish's skin;
3. Ethylene vinyl acetate copolymer pellets containing a fish GnRH analog (GNRHH) - [D-Arg$^6$-Pro$^9$-NET]sGnRH (150 mg/fish 150 μg/fish), implanted under the skin;
4. Injection of saline.

All fish were bled before and at different intervals after hormone administration, for the determination of blood GtH levels, similarly as in Example 1.

An additional four groups of 20 females in each group, undergoing advanced stages of vitellogenesis, were treated as above and used for monitoring the state of ovarian development and the occurrence of ovulation. An overian biopsy was sampled from these females every 2 to 4 days for 30 days post-treatment.

GtH levels in the plasma of fish receiving treatment No. 4 (control) remained low, whereas the level in those receiving treatment No. 1 surged for a short period (about 48 hrs.). The GtH level in the two groups of fish receiving treatment No. 2 or 3 was elevated over a prolonged period (more than 1 week).

The degree of ovulation (in percent of ovulated females) of the various groups of fish, is shown in the following Table I:

TABLE 1

| Days post treatment: | 6 | 9 | 30 |
|---|---|---|---|
| Group 1 | 30 | 40 | 60 |
| Group 2 | 90 | 100 | |
| Group 3 | 85 | 100 | |
| Group 4 | 20 | 30 | 75 |

The injection of GnRHa did not accelerate or synchronize ovulation, as evidenced by the fact that the proportion of ovulated females in the injected group (Group No. 1) did not differ from that observed in the control group (Group No. 4). In contrast, the administration of GnRHa in a carrier which gradually releases the active compound in a controlled manner, whether a biodegradable carrier (Group No. 2) or a carrier which releases the active compound by diffusion (Group No. 3), significantly advanced and accelerated ovulation: all treated females in these groups ovulated by 9 days post-treatment.

The above results demonstrate the efficacy of the treatment in accordance with the method of the present invention in inducing a sustained high GtH blood level which causes ovulation which will eventually end in spawning. The rapidity with which ovulation occurs, ensures also the relative synchronicity of the subsequent spawning.

SUMMARY

The results described in the above examples were obtained from three entirely different fish species. The treatment in accordance with the invention for the manipulation of reproduction was shown to be effective in all those species and thus it is proof of the applicability of the method in accordance with the invention in aquaculture of all fish.

I claim:

1. A method for the induction and synchronization of ovulation, spawning, sperm production and spermiation in fish, which comprises administering to the fish an effective amount of an active compound selected from the group consisting of GnRH, LHRH, GnRH analogs, LHRH analogs and non-toxic salts of any of those compound, wherein said active compound is embedded in a biodegradable polymer based carrier matrix, and wherein said carrier matrix is (i) biocompatible with said fish and said active compound and (ii) confers sustained release properties on said active compound when said composition is administered to said fish.

2. A method according to claim 1, wherein said carrier comprises a natural polymer.

3. A method according to claim 2, wherein said polymer is a polysaccharide or a protein.

4. A method according to claim 1, wherein said carrier comprises a synthetic polymer.

5. A method according to claim 4, wherein said carrier is a polymer selected from the group consisting of polylactic polyglycolic acid, polyanhydrides, polyorthoesters and polycaprolactone.

6. A method according to claim 1, which comprises administering also an effective amount of dopamine.

7. A method according to claim 1, performed outside the natural spawning season and which comprises also administering the male fish with an effective amount of said active compound embedded in said carrier matrix.

8. A method according to claim 1, wherein said active compound embedded in said carrier matrix is implanted in said fish.

9. A method according to claim 1, wherein said active compound embedded in said carrier matrix is injected in said fish.

* * * * *